US008241886B2

(12) United States Patent
Truong-Le et al.

(10) Patent No.: US 8,241,886 B2
(45) Date of Patent: Aug. 14, 2012

(54) FORMULATIONS FOR PRESERVATION OF ROTAVIRUS

(75) Inventors: Vu Truong-Le, Campbell, CA (US); Luisa Yee, Los Altos, CA (US); David Lechuga-Ballesteros, San Jose, CA (US); Satoshi Ohtake, Milpitas, CA (US)

(73) Assignee: Aridis Pharmaceuticals, San Jose, CA (US)

( * ) Notice: Subject to any disclaimer, the term of this patent is extended or adjusted under 35 U.S.C. 154(b) by 218 days.

(21) Appl. No.: 12/733,920

(22) PCT Filed: Sep. 24, 2008

(86) PCT No.: PCT/US2008/011169
§ 371 (c)(1),
(2), (4) Date: Mar. 25, 2010

(87) PCT Pub. No.: WO2009/042202
PCT Pub. Date: Apr. 2, 2009

(65) Prior Publication Data

US 2010/0226939 A1 Sep. 9, 2010

Related U.S. Application Data

(60) Provisional application No. 60/995,291, filed on Sep. 25, 2007.

(51) Int. Cl.
*C12N 7/00* (2006.01)
*A61K 39/15* (2006.01)

(52) U.S. Cl. .................................. 435/235.1; 424/215.1

(58) Field of Classification Search ........................ None
See application file for complete search history.

(56) References Cited

U.S. PATENT DOCUMENTS 6,616,931 B1 9/2003 Burke
6,630,169 B1 * 10/2003 Bot et al. ...................... 424/489

FOREIGN PATENT DOCUMENTS

WO WO 2006/087205 A1 8/2006
WO WO 2007/020078 A2 2/2007

OTHER PUBLICATIONS

Clark et al. (2003) "Safety, immunogenicity and efficacy in healthy infants of G1 and G2 human reassortant retavirus vaccine in a new stabilizer/buffer liquid formulation." *The Pediatric Infectious Disease Journal*, 22(10): 914-920.
EP Search Report from Application No. 08834341.3, (2012).
Shirley et al. (1981) "The Influence of Divalent Cations on the Stability of Human Rotavirus." *Archives of Virology*, 67: 1-9.

* cited by examiner

*Primary Examiner* — Stacy B. Chen
(74) *Attorney, Agent, or Firm* — Quine Intellecutal Property Law Group, P.C.

(57) ABSTRACT

This invention provides formulations and methods for stabilizing viruses in liquid and dried formulations. In particular, formulations are provided including $Zn^2$+ cations that stabilize the viability of Rotaviruses. Methods of vaccination include neutralization of gastric contents and administration of the vaccine formulations of the invention.

22 Claims, 3 Drawing Sheets

FORMULATIONS FOR PRESERVATION OF ROTAVIRUS

CROSS-REFERENCE TO RELATED APPLICATIONS

This application is a 371 application of PCT/US08/011,169, filed Sep. 24, 2008, and claims priority to and benefit of a prior U.S. Provisional Application No. 60/995,291, Formulations for Preservation of Rotavirus, by Vu Truong-Le, et al., filed Sep. 25, 2007. The full disclosure of the prior application is incorporated herein by reference.

FIELD OF THE INVENTION

The present invention is in the field of formulation and stabilization of live viral vaccines. In particular, the invention is directed to, e.g., methods and formulations containing combinations of constituents useful in retaining viability of Rotavirus liquid, dried or lyophilized vaccines.

BACKGROUND OF THE INVENTION

Available commercial Rotavirus liquid oral vaccines are required to be stored under refrigerated conditions. This constitutes a significant logistic issue when the vaccine is needed in areas where refrigeration is not widely available. Furthermore, the vaccines are not sufficiently stable to resist further manufacturing processes that may be involved in final dosage presentations.

Rotaviruses can cause acute gastroenteritis, which frequently requires hospitalization of infants and young children in developed countries, and is a common cause of death in children less than 5 years of age in developing regions of the world. Studies in the developed world have demonstrated that between 34 and 63% of hospitalizations of children for acute diarrheal disease are associated with Rotavirus infection. Rotaviruses are also responsible for substantial proportion of the mortality associated with diarrheal diseases in third world countries. An effective Rotavirus vaccine would therefore have a major impact on the health of children in both the developed and developing areas of the world.

Rotaviruses are double stranded RNA viruses with an inner and outer capsid. Several serotypes have been defined by plaque reduction neutralization tests, and studies of reassortant viruses have demonstrated that two outer capsid proteins, VP7 and VP4, are the determinants of virus serotype. The gene segments encoding the VP7 and VP4 proteins segregate independently, so it has been proposed that serotyping nomenclature should include both the G type, determined by VP7, and the P type, determined by VP4. Most human rotavirus infections in the U.S. are caused by viruses of G types 1, 2, 3, or 4, and P types 1, 2, or 3. However, other human rotavirus types, including for example, type G9, are more prevalent in Asia, Europe and certain third world countries.

In U.S. Pat. No. 6,616,931, Rotavirus Vaccine Formulations, to Burke, et al., liquid and lyophilized formulations of vaccines against rotavirus infection and methods of their preparation were described. The formulations include sugars and buffering agents appropriate for oral administration of Rotavirus vaccines. For some serotypes, Burke has found Rotaviruses can remain viable longer in liquid formulations containing about 50% of sugars, a phosphate buffer, and a carboxylate, at about neutral pH. For some serotypes, Burke has found Rotaviruses can remain viable longer in lyophilized cakes dried from formulations containing about 5% of sugars, a phosphate buffer and human serum albumin. However, Burke teaches that the presence of zinc ions dramatically reduce the viability of Rotaviruses in the presence or absence of calcium ions.

In view of the above, a need exists for liquid Rotavirus live vaccines that remain viable for extended periods at room temperature. It would be desirable to have methods of Rotavirus vaccination that allow the vaccine to retain additional viability in transport and storage. The present invention provides these and other features that will be apparent upon review of the following.

SUMMARY OF THE INVENTION

The novel inventions provide methods and compositions for stabilization of viruses. In particular, the compositions employ $Zn^{2+}$, in combination with various other formulation constituents, to stabilize Rotavirus in live oral vaccine formulations. Methods of the invention include administration of the oral vaccines to individuals in need, e.g., after neutralization of their gastric contents.

In one aspect of vaccine compositions, the liquid vaccine formulation includes at least one strain of Rotavirus at a titer ranging from about $1\times10^5$ to about $1\times10^8$ pfu/mL, a sugar at a concentration ranging from about 10% to about 60% (w/v), a buffer ranging in concentration from about 10 mM to about 2 M, a carboxylate ranging in concentration from about 50 mM to about 2 M, and $Zn^{2+}$ in a concentration ranging from about 0.5 mM to 20 mM. In preferred embodiments, particularly where excursions to high temperatures are expected, the formulation can further include $Ca^{2+}$ in a concentration ranging from about 0.5 mM to 20 mM. In many cases, benefits can be derived from providing the formulation with from about 0.5% to about 5% of gelatin. In preferred embodiments of the vaccine formulations, the concentration of sugar is between about 20% to about 40%, the concentration of phosphate is between about 0.05 to about 0.3 M, and the carboxylate is a citrate or a succinate at a concentration between about 0.05 M and about 0.7 M.

Particular constituents or proportions of constituents are identified herein as useful aspects of the compositions. For example, the carboxylate of the formulation can be a succinate, citrate, fumarate, tartarate, maleate, lactate, and for the like. In some embodiments, the carboxylate is a phosphate in a buffer system similar to a citric-phosphate buffer system. Other preferred sources of phosphate include, e.g., a monophosphate, a polyphosphate and a phosphorylated compound (such as, e.g., phosphorylated sugars or phosphorylated sugar acids). For enhanced stability of Rotaviruses, the preferred formulation pH can range from about pH 5.0 to about pH 8.0; more preferably from pH 6.0 to pH 6.5. In other aspects of the invention, the sugar can include sucrose, mannitol, lactose, sorbitol, dextrose, fucose, trehalose, polyaspartic acid, inositol hexaphosphate (phytic acid), sialic acid and N-acetylneuraminic acid-lactose, and/or the like. In other aspects, the vaccine formulation is a suspension of solution in a diluent, such as, e.g., a tissue culture medium, saline, water, and/or the like.

In some cases, the formulations can usefully include from about 0.001% to about 2% of a nonionic surfactant. For example, the formulations can include nonionic surfactants, such as, a polysorbate, a polyoxyethylene alkyl ether, a nonaethylene glycol octylphenyl ether, a hepatethylene glycol octylphenyl ether, a sorbitan trioleate, a polyoxyethylene-polyoxypropylene block copolymer and/or PLURONIC F68™. In preferred embodiments, the surfactant is present in the formulation at a concentration ranging from about 0.005% to about 0.1%.

In a most preferred embodiment, the liquid vaccine formulation comprises at least one strain of rotavirus at a titer ranging from about $1\times10^5$ to about $1\times10^7$ pfu/mL, a sugar at a concentration ranging from about 15% to about 30% (w/v), a phosphate buffer ranging in concentration from about 40 mM to about 100 mM, a carboxylate ranging in concentration from about 40 mM to about 300 mM, and $Zn^{2+}$ in a concentration ranging from about 2 mM to 5 mM, and with a formulation pH ranging from about pH 6.0 to about pH 6.5.

The present invention includes methods of preparing oral vaccine formulations and methods of administering the vaccines. For example, a method of preparing a vaccine can include cultivating the Rotavirus. The virus (inactivated or preferably as a live or attenuated virus) can be formulated as an active constituent into a formulation for oral administration. The final formulation can be any of those described herein, e.g., comprising the Rotavirus at a titer ranging from about $1\times10^5$ to about $1\times10^8$ pfu/mL, a sugar at a concentration ranging from about 5% to about 40% (w/v), a pH buffer ranging in concentration from about 10 mM to about 2 M at a pH ranging from about pH 5 to about pH 7, and $Zn^{2+}$ in a concentration ranging from about 0.5 mM to 20 mM. In a preferred embodiment, the formulation $Zn^{2+}$ has a concentration of about 4 mM. In many embodiments, the formulation can also include $Ca^{2+}$ at a concentration ranging from about 0.5 mM to 20 mM. Other aspects of the formulations for use in the methods include, e.g., the presence of from about 0.5% to about 5% of gelatin, from about 0.001% to about 2% of a nonionic surfactant, from about 0.05 M to about 2 M of a carboxylate and/or from about 0.1% to about 1.25% of at least one amino acid selected from the group consisting of: glutamate, glutamine and arginine.

The present methods include ways to prepare dry versions of the formulations. That is, the formulations of the invention can be dried to form vaccines for storage and/or administration in non-liquid form. In one aspect, the methods further include the step of lyophilizing the liquid formulation, e.g., to form a dry powder or cake. In another aspect, the liquid formulation can be spray dried to form powder particles, to form a dried foam or to form a dried layer on a surface.

Oral Rotavirus vaccine of the invention can be administered to individual in need. For example, the individual's stomach pH can be raised by orally administering a pH buffer. Concurrent with or after raising the pH, the vaccine comprising at least 0.5 mM $Zn^{2+}$ can be orally administered to the individual.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "sugar" can include mixtures of sugars, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

The term "about", as used herein, indicates the value of a given quantity can include quantities ranging within 10% of the stated value, or optionally within 5% of the value, or in some embodiments within 1% of the value.

A "diluent", as used herein, refers to a liquid or solution into which recited formulation constituents are solutes in the liquid formulations of the invention.

The term "cultivating", as used herein, refers to culturing a virus in an appropriate host cell.

The term "neutralizing", as used herein with regard to stomach acid, refers to raising the stomach digestive juices to pH 4 or above. Preferably, neutralizing in this context refers to raising the stomach digestive juices to a pH of about 6 or above.

BRIEF DESCRIPTION OF THE DRAWINGS

FIG. 1 is a chart showing maximum Rotavirus capsid robustness to temperature (extended relatively dark zone) in the region of pH 6 and 7. Relatively dark band in the lower pH 6 and 7 zones signals robustness to temperature for key molecular properties.

FIG. 2 shows the data of FIG. 1 in a graphic form.

FIG. 3 presents charts of UV circular dichroism versus temperature for Rotavirus in formulations at various pHs.

DETAILED DESCRIPTION

The present invention is the result of extensive experimentation to identify new combinations of vaccine formulation constituents and proportions of constituents. In particular, we have surprisingly found that liquid formulations for Rotavirus vaccines containing $Zn^{2+}$, but not necessarily $Ca^{2+}$, can provide highly stable live vaccines in combination with, e.g., buffers, sugars and polymers, as described herein.

In one embodiment of liquid Rotavirus vaccine formulations, the viability of attenuated virus is enhanced in the presence of $Zn^{2+}$ salts. For example, Rotavirus viability can be extended in room temperature storage in a liquid formulation containing a high concentration of sugars, a phosphate buffer at a pH near pH 6, gelatin and $Zn^{2+}$ salts.

Methods of inoculating individuals with a liquid Rotavirus vaccine can include providing a liquid vaccine formulation including $Zn^{2+}$ for oral administration in combination with an ingestible pH buffer. The pH buffer should have the capacity to raise the pH of the individual's gastric juices above about pH 4 before or during administration of the liquid Rotavirus vaccine.

Liquid Rotavirus Vaccines

The liquid oral Rotavirus vaccines of the invention include, e.g., $Zn^{2+}$ in combination with other constituents found to compliment stability in the presence of $Zn^{2+}$. For example, the liquid vaccines can include any of: 1) substantial amounts of a sugar; 2) a pH buffer; 3) a carboxylate; 4) a soluble protein; 5) amino acids; and/or, 6) $Ca^{2+}$ ions. Particularly stabilizing formulations include combinations of $Zn^{2+}$, sucrose, gelatin and phosphate at about pH 6.

Sugars

Rotavirus were found to be more stable in the presence of substantial amounts of polyol, such as a substantially water soluble sugar. In one aspect, the sugar is present in a amount ranging from about 10% to 70%, by weight. In preferred embodiments, the sugar is present in the liquid formulation in the range between 10% and 70%, 20% and 60%, 30% and 50%, or about 40% by weight. In preferred embodiments the sugars are present in the formulations at a concentration ranging from about 20% to about 30% by weight.

More preferred sugars include, e.g., sucrose, mannitol, lactose, sorbitol, dextrose, fucose, trehalose, polyaspartic acid, inositol hexaphosphate (phytic acid), sialic acid and N-acetylneuraminic acid-lactose. In a typical embodiment, the sugar is sucrose at about 40% of the liquid formulation by weight. In preferred embodiments, the formulation sugar is a monosaccharide or disaccharide.

pH

Studies showed desirable stability qualities, at ambient temperatures or less, for Rotavirus as pH ranging from pH 5 to 7. See circular dichroism analysis result shown in FIGS. 1 and 2, and static light scattering analysis shown in FIG. 3. Protein molecular analytical assays involving far UV-circular dichroism (CD), static light scattering, microcalorimetry, pH dependent fluorescence emission spectral analysis, and Laurdan polarization analysis were used to determine the pH and ionic strength conditions where live rotavirus (G1 and G3 strains) would be most stable for further addition of stabilizers. Live rotavirus were found most stable at a pH range of 6.0 to 6.5. A preferred pH to enhance stability of Rotavirus capsids was identified around pH 6.3.

In some embodiments of the invention, the buffer for pH control in stability of the virus can also act as a pH buffer to raise the pH gastric juices when the vaccine is administered to an individual. In such a case, it can be preferred that the buffer be at a higher concentration and on the high side of preferred pH values. For example, it can be desirable to have total buffer capacity of the formulation be at least a milliequivalent per liter, (mEq/L), preferably 10 mEq/L or more, 20 mEq/L, 50 mEq/L, 100 mEq/L, 500 mEq/L, 1000 mEq/L, 2000 mEq/L or more. In some embodiments, the buffer capacity can be lower where an antacid is administered separately to the patient in need from administration of the oral vaccine. It is preferred that the buffering capacity of an individual dose to raise a patient's gastric juices range from about 0.5 mEq to 4 mEq, from 0.8 mEq to 2 mEq or about 1 mEq. Preferably, where an individual is to be administered the vaccine without a separate buffer composition, the oral vaccine provides adequate buffering capacity to raise the individual's gastric cavity to a pH of 4 or higher.

Polymers

Formulations of the invention, e.g., comprising $Zn^{2+}$, appear to benefit from the presence of a polymer in the formulation. In preferred embodiments, the polymer is ingestible. Preferably, the polymer has significant ionic character, preferably anionic character. In certain embodiments, the polymer is present in a concentration ranging from about 1% to 4% by weight, or about 2% of the liquid formulation by weight.

In one embodiment, the polymer is gelatin. In certain embodiments, the liquid formulation comprises 1% or 2% gelatin or hydrolyzed gelatin, by weight.

Amino Acids

Zwitterions can help stabilize protein structures and contribute to pH buffering. In some embodiments of the invention amino acids are present in the formulation in amounts ranging from about 0.1% to 4% by weight. In preferred embodiments, one or more amino acids are present at a concentration of from 0.5% to 1.5%, or about 1% of the liquid formulation by weight.

Preferred amino acids for incorporation into the inventive formulations are, e.g., arginine, lysine, methionine, histidine, glutamic acid, and/or the like. In a most preferred embodiment, the amino acid is arginine, e.g., at a concentration near 1% by weight or the liquid vaccine formulation.

Divalent Cations

Most preferred embodiments of the present inventive formulations include the presence of $Zn^{2+}$ ions. This, even though the presence of $Zn^{2+}$ is taught as accelerating virus inactivation in the prior art (see, e.g., U.S. Pat. No. 6,616,931, Example 2a—"Effect of Divalent Metal Ions"). On the contrary, we have found that the presence of $Zn^{2+}$ in liquid Rotavirus vaccines enhances the stability of virus viability. See Tables 1 to 3.

In preferred embodiments, oral liquid Rotavirus vaccines of the invention include zinc ions. It is desirable that the $Zn^{2+}$ be present at a concentration of at least 0.5 mM. It is preferred that $Zn^{2+}$ be present at a concentration ranging from about 1 mM to about 20 mM, from about 2 mM to about 10 mM, from about 3 mM to about 6 mM zinc ions, or about 4 mM zinc ions.

The formulations can include other divalent metal cations. For example, the formulations can include $Zn^{2+}$ in combination with other cations, such as, e.g., $Ca^{2+}$. Particularly, for storage of liquid formulations at high temperatures (above room temperature), the combination of $Zn^{2+}$ and $Ca^{2+}$ can enhance stability (see Table 2, line RVLQ-13 $Ca^{2+}$ and RVLQ-14 $Ca^{2+}/Zn^{2+}$). However, at more typical storage temperatures of about 25° C. (essentially "room temperature"), formulations with $Zn^{2+}$ alone appear to be more stable than formulations with no divalent cations or with only $Ca^{2+}$. For some formulations, particularly for certain storage conditions, it can be beneficial to have a combination of both $Zn^{2+}$ and $Ca^{2+}$ ions in the liquid formulation.

Preferred Combinations of Constituents

Certain combinations of formula constituents are more effective in stabilizing Rotavirus in the presence of $Zn^{2+}$; these combinations were not identified through mere optimization of result-effective variable because, e.g., the discovery required analysis across multiple variables (not known to be result-effective in this context) and by adjustment of multiple constituent proportions in parallel. Further, the prior art teaches away from the present invention, so elucidation of the present formulations can not be considered optimization of a known result-effective variable.

Preferred combinations of excipient constituents to stabilize liquid formulations of viable Rotavirus vaccine include, e.g., combinations of $Zn^{2+}$, a polymer, a sugar and a buffer at about pH 6. In more preferred embodiments, the sugar can be sucrose at a concentration of about 20% by weight. More preferred embodiments can include the polymer comprising gelatin, the gelatin being at a concentration of about 2% by weight. More preferred embodiments can include the $Zn^{2+}$ at a concentration of about 4 mM. More preferred embodiments can include the pH at about pH 6.3. More preferred embodiments, particularly for formulations expected to be exposed to higher temperatures, can include $Ca^{2+}$ ions, preferably at a concentration of about 4 mM.

In addition to the above combinations of constituents, it can be beneficial to include a carboxylic acid, such as succinate or citrate, e.g., at a concentration ranging from about 0.2% to about 2%, or about 1% by weight.

In addition to the combinations of constituents described above, it can be beneficial to include a buffer salt, such as a phosphate buffer pair, e.g., at a concentration ranging from about 50 mM to 250 mM or about 150 mM. Such buffers can act to reduce stomach acidity and protect virus viability as the vaccine passes through the stomach.

In the present inventive formulations, the presence of nonionic detergents can possibly enhance stability. However, in many cases, the presence of non-ionic detergents can have no affect or reduce stability of the virus in storage. The present invention can include non-ionic detergents, or not.

Methods of Stabilizing Rotavirus Vaccine Formulations

The present invention includes methods of stabilizing oral Rotavirus vaccine formulations and methods of administering a Rotavirus vaccine. For example, the methods for stabilizing a Rotavirus vaccine can include preparation of a formulation comprising the unique combination of constituents and parameters described herein. Methods of administration typically involve preparing an oral Rotavirus vaccine including functional amounts of $Zn^{2+}$, neutralizing the gastric juices of the individual in need of the vaccination, and orally administering the vaccine.

In one embodiment, a rotavirus in a liquid vaccine formulation is prepared and stabilized by cultivating the rotavirus and formulating it to provide a liquid formulation of the rotavirus at a titer ranging from about $1 \times 10^5$ to about $1 \times 10^8$ pfu/mL in a formulation comprising a sugar at a concentration ranging from about 5% to about 60% (w/v), a pH buffer ranging in concentration from about 10 mM to about 2 M at a pH ranging from about pH 5 to about pH 7, and $Zn^{2+}$ in a concentration ranging from about 0.5 mM to 20 mM.

Administering an oral rotavirus vaccine to an individual can include the steps of neutralizing the individual's stomach acid by orally administering a pH buffer to the individual, and orally administering the rotavirus vaccine, which includes at least 0.5 mM $Zn^{2+}$.

The stable formulations of the methods can be prepared to provide any of the formulations described in the Liquid Rotavirus Vaccines section, above. For example, the formulations can include: a Rotavirus, a sugar, a buffer, $Zn^{2+}$, a polymer, a carboxylate, a surfactant and/or and a diluent. In preferred embodiments of the methods, the formulation is prepared to include at least $1 \times 10^5$ pfu/mL of a Rotavirus, at least 20% sugar by weight, at least 100 mM phosphate buffer (about pH 6), and at least 2 mM $Zn^{2+}$.

Rotavirus can be formulated into the stable formulations by any appropriate techniques known in the art. For example, cultivated virus can be purified or enriched from a culture media and blended with concentrated formulations with an additional diluent quantity sufficient to provide the desired constituent concentrations, as is known in the art. Alternately, the virus can be formulated directly into culture media containing the virus by addition of individual constituents in solid or liquid concentrate form. Optionally, a solution or suspension containing the virus can be dialyzed against a volume of liquid containing the chemical constituents of the stabilizing formulation, thus providing the virus in the desired formulation.

Administering the oral virus can include oral administration of the stabilized vaccine to an individual. In many cases, the gastric juices of the individual are increased from the typical acidic stomach pH (often between pH 1.5 and pH 3) to a pH at least of pH 4. This can be accomplished by administration of an antacid, such as calcium carbonate or magnesium carbonate, before or during administration of the vaccine. Optionally, the vaccine itself can be formulated to include sufficient pH buffer capacity to raise the individual's stomach interior above pH 4. In preferred embodiments, the individual's stomach pH is raised to about pH 6 to pH 7.

In some embodiments of the invention, the Rotavirus vaccine is prepared in a solid or semisolid form. For example, liquid formulations of the invention can be spray dried to form powder particles. The formulations can be lyophilized to provide readily reconstituted powders or cakes. The formulations can be sprayed onto a surface to form a dry layer. The dry formulations can be compressed into pill form. In many dry formulation embodiments the liquid formulation to be dried includes a polymer to provide structural strength to the dried material, to provide protection through the stomach of a patient, and/or to provide a timed release of the viable viruses.

EXAMPLES

The following examples are offered to illustrate, but not to limit the claimed invention.

Example 1

Multiple Formulation Parameters for Stabilization of Rotavirus

Combinations of various formulation constituents and various formulation working parameters were prepared to evaluate Rotavirus stability in formulations for oral vaccines.

Figure 1:
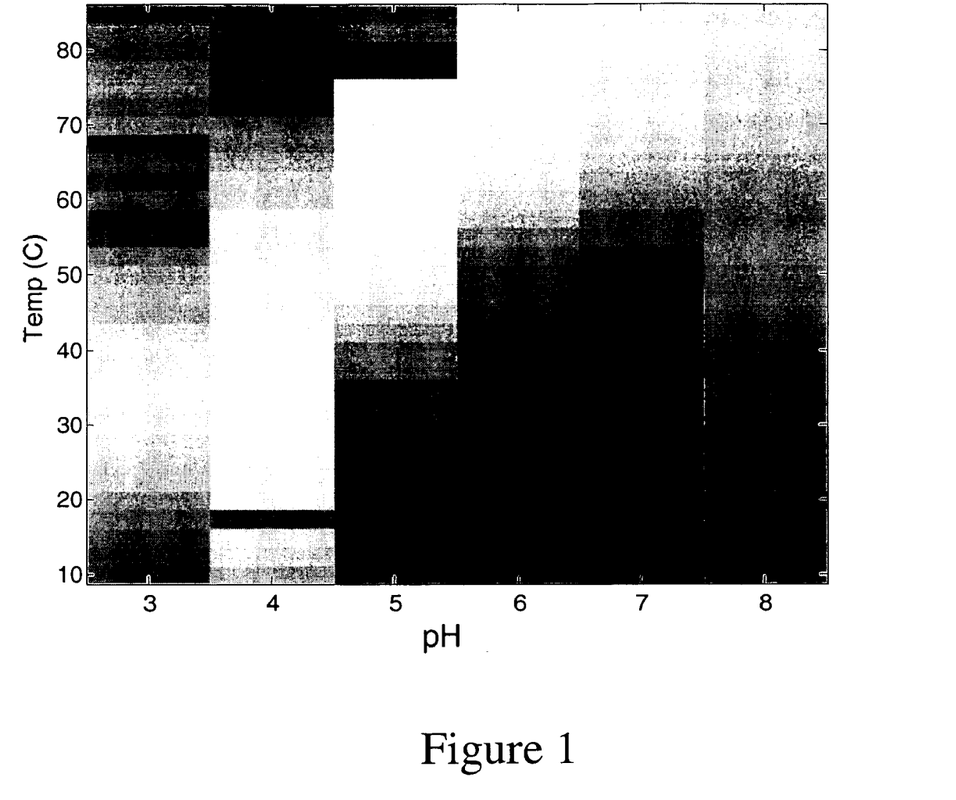
Figure 2:
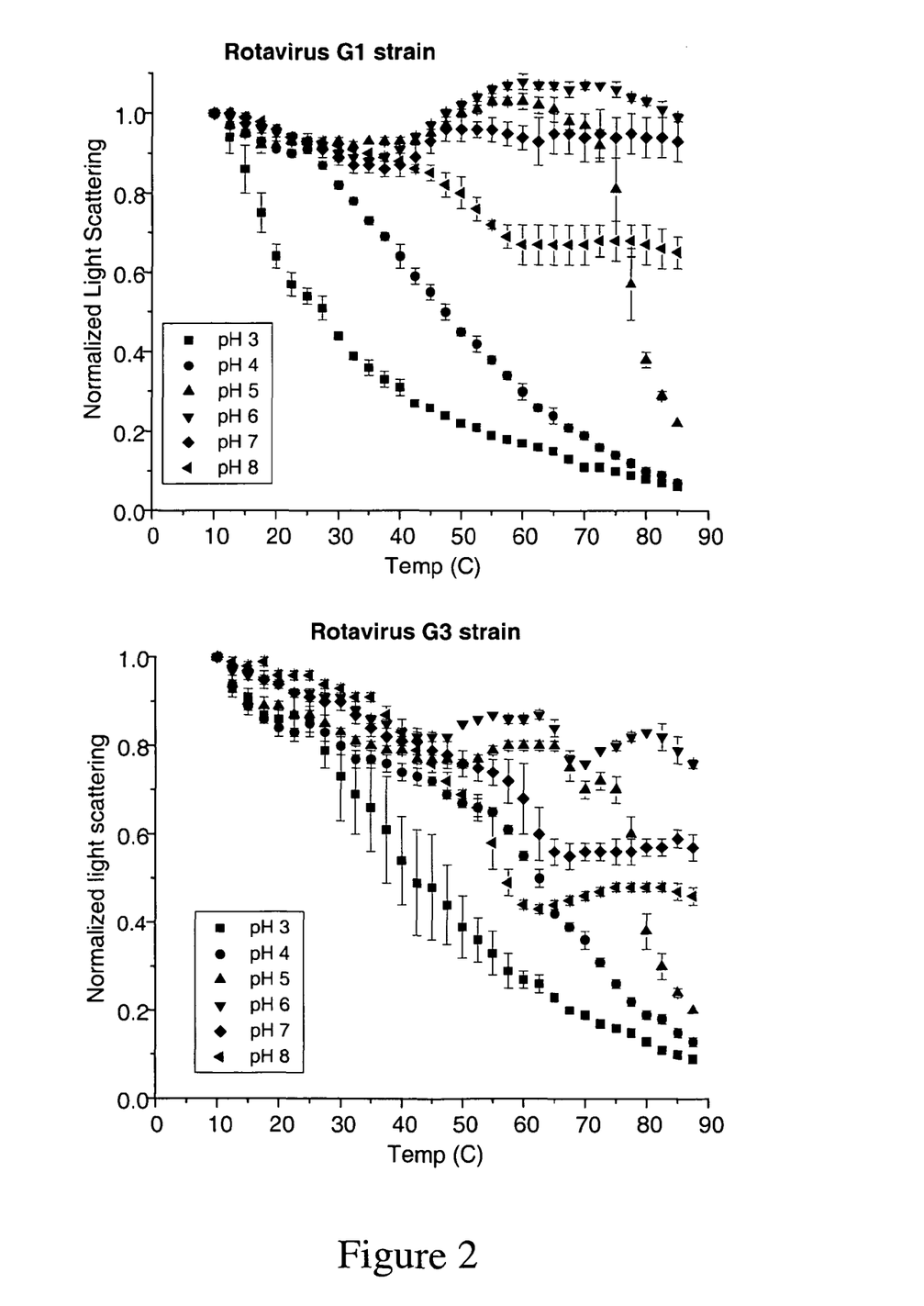
Figure 3:
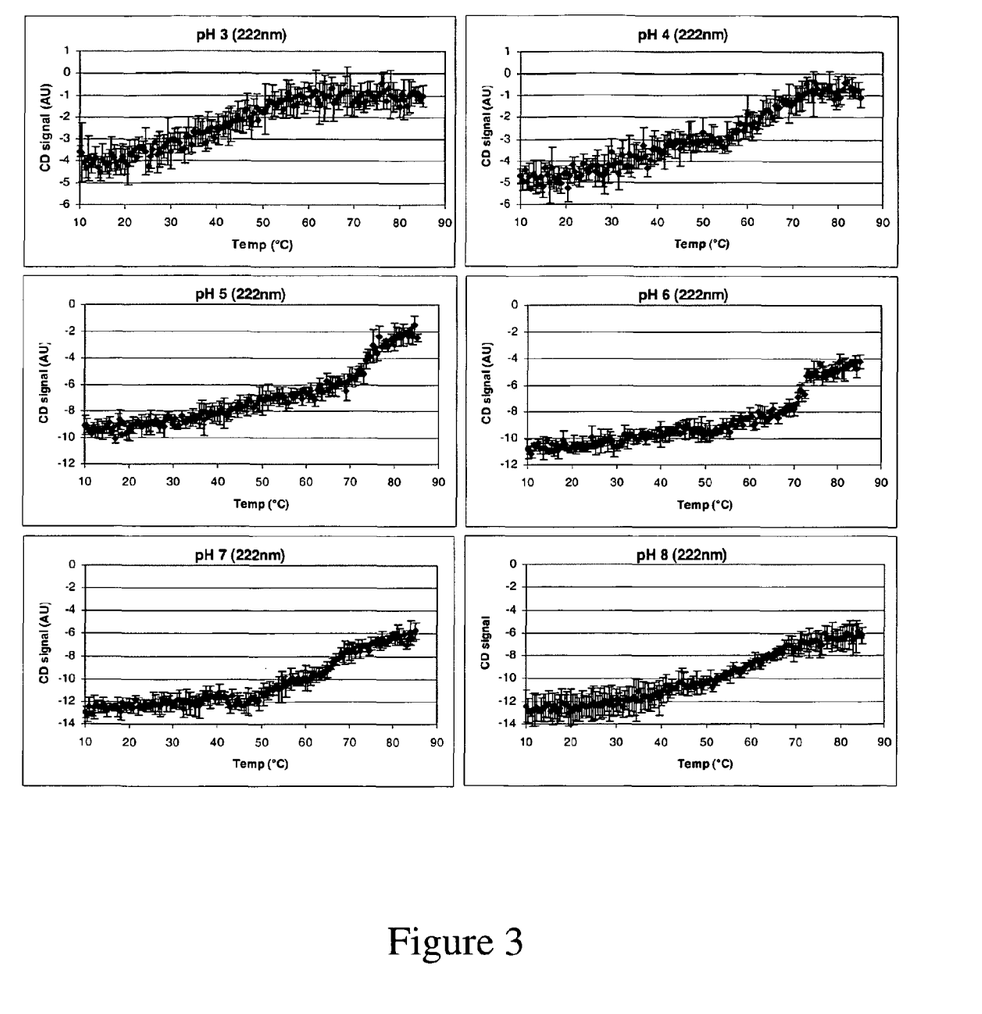

As an initial step, we evaluated Rotavirus stability with regard to pH. As shown in FIGS. 1 and 2, a preferred formulation space is located in extended relatively dark zones having maximum robustness against thermal degradation in the region of pH 6 and 7. The dark band is based on signal robustness to temperature for key molecular properties. As shown in FIG. 2, pH study results are corroborated by circular dichroism (CD) data. The CD data versus temperature at various pHs suggested the Rotavirus proteins are most stable (least changed) at a pH between 6 and 7.

Using formulations in the identified pH range of maximum stability, a variety of additional parameters were evaluated in a matrix of experiments. For example, at pH 6.3, Rotaviruses were blended to provide a variety of formulations having various ranges of sugar concentrations, polymer concentrations, and unique combinations of constituents. See Table 1. Of note are the formulations including 0, 1 or 2 divalent metallic cations. A series of Rotavirus liquid formulations based on various excipients (e.g. sucrose, potassium phosphate dibasic, citric acid, etc.) shown in Table 1 were prepared and tested, e.g., for initial viability and stability in storage.

TABLE 1

Rotavirus Liquid Formulations
(pH 6.3 citric acid/potassium phosphate dibasic buffer 0.8 mEq)

| Component | Formulation # | | | | | | | | | | | | | | | | | | | | | | |
|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 14a | 15 | 16 | 17 | 18 | 19 | 20 | 22 | 23 |
| G3 strain | x | x | x | x | x | x | x | x | x | x | x | x | x | x | | | | | | | | | |
| G1 strain | | | | | | | | | | | | | | | x | x | x | x | x | x | x | x | x |
| Sucrose 7% | x | | | | | | | | | | | | | | | | x | | | | | | |
| Sucrose 20% | | x | | | | | | | | | | | | | | | | x | | | | | |
| Sucrose 30% | | | x | | | | | | | | | | | | | | | | x | | | | |

TABLE 1-continued

Rotavirus Liquid Formulations
(pH 6.3 citric acid/potassium phosphate dibasic buffer 0.8 mEq)

| Component | Formulation # | | | | | | | | | | | | | | | | | | | | | | |
|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 14a | 15 | 16 | 17 | 18 | 19 | 20 | 22 | 23 |
| Sucrose 40% | | | | x | x | x | x | x | x | x | x | x | x | x | x | | | | x | x | x | x | x |
| Gelatin 1% | | | | | x | x | x | | | | | | x | x | x | x | x | x | | x | | | x |
| Gelatin 2% | | | | | | | | x | x | x | x | | | | | | | | | | x | | |
| Arginine HCl 1.2% | | | | | x | x | | x | | | | | | | | | | | | x | | | x |
| Pluronic F-68, 0.1% | | | | | | | x | | | x | x | | | | | | | | | | | | |
| ZnCl$_2$, 2 mM | | | | | | | | | | | | | | | | | | | | | x | | |
| ZnCl$_2$, 4 mM | | | | | x | x | x | x | x | x | x | x | | x | x | x | x | x | x | x | | x | x |
| CaCl$_2$, 2 mM | | | | | | | | | | | | | | | | | | | | | x | | |
| CaCl$_2$, 4 mM | | | | | | | | | | | | x | x | x | x | x | x | x | x | x | | x | x |

The formulations described herein were evaluated for the stabilization of live Rotavirus. The stabilizing formulation components include various excipients with the addition of a combination of divalent ions, specifically a mixture containing divalent zinc ($Zn^{2+}$) and/or divalent calcium ($Ca^{2+}$).

Stability data of all formulation combinations stored at 37° C., 25 and 4° C. are show in Table 2.

TABLE 2

Rotavirus G3 strain liquid formulations stability slopes
(log ffu/month ± SE). Initial target titer 5.84 log ffu/ml

| Formulation | After 2 months at 37° C. | After 9 months at 25° C. | After 9 months at 4° C. |
|---|---|---|---|
| RVLQ-01 | >3 | −0.65 ± 0.07 | −0.01 ± 0.03 |
| RVLQ-02 | >3 | −0.59 ± 0.10 | −0.01 ± 0.03 |
| RVLQ-03 | >3 | −0.20 ± 0.03 | −0.02 ± 0.05 |
| RVLQ-04 | >3 | −0.18 ± 0.02 | −0.03 ± 0.04 |
| RVLQ-05 | >3 | −0.10 ± 0.02 | −0.02 ± 0.05 |
| RVLQ-06 | >3 | −0.04 ± 0.04 | −0.03 ± 0.04 |
| RVLQ-07 | >3 | −0.02 ± 0.04 | −0.02 ± 0.04 |
| RVLQ-08 | >3 | −0.02 ± 0.03 | −0.02 ± 0.05 |
| RVLQ-09 | >3 | −0.01 ± 0.06 | −0.02 ± 0.04 |
| RVLQ-10 | >3 | −0.01 ± 0.04 | −0.04 ± 0.04 |
| RVLQ-11 | >3 | −0.09 ± 0.03 | −0.01 ± 0.03 |
| RVLQ-12 | >3 | −0.12 ± 0.03 | −0.01 ± 0.04 |
| RVLQ-13 | −0.84 ± 0.17* | −0.13 ± 0.02 | −0.05 ± 0.02 |
| RVLQ-14 | −0.99 ± 0.06* | −0.03 ± 0.03 | −0.02 ± 0.02 |
| RVLQ-14a | 0.42 ± 0.19 | −0.560 ± 0.020 | No change |
| RVLQ-15 | >3 | −0.066 ± 0.022 | No change |
| RVLQ-16 | 0.82 ± 0.11 | −0.071 ± 0.026 | No change |
| RVLQ-17 | 0.75 ± 0.11 | −0.076 ± 0.016 | No change |
| RVLQ-18 | 0.66 ± 0.16 | −0.059 ± 0.017 | No change |
| RVLQ-19 | 0.89 ± 0.16 | −0.067 ± 0.017 | No change |
| RVLQ-20 | 1.62 ± 0.22 | −0.115 ± 0.032 | No change |
| RVLQ-22 | 0.40 ± 0.18 | −0.049 ± 0.011 | No change |
| RVLQ-23 | 0.64 ± 0.12 | −0.045 ± 0.037 | No change |

*@ 1.8 months

Contrary to what it has been previously reported (U.S. Pat. No. 6,616,931, at Example 2) a synergistic effect (see Table 3 formulations RVLQ-13 $Ca^{2+}$ and RVLQ-14 $Ca^{2+}$ plus $Zn^{2+}$) between $Zn^{2+}$ and $Ca^{2+}$ to inhibit the inactivation of Rotavirus was observed, resulting in highly thermostable stable liquid formulations at 37° C. At lower temperatures, addition of $Ca^{2+}$ and/or $Zn^{2+}$ provided the most stable formulations.

Formulations containing $Ca^{2+}$ and/or $Zn^{2+}$ appear to inhibit the inactivation of rotavirus as shown by the decrease in the log loss of the viral titer after the indicated time at 37° C. When salts of divalent cations $ZnCl_2$ and/or $CaCl_2$ were added to the high sucrose base formulation, an increase in stability at 37° C. was observed. Such formulations exhibited a loss of activity of less than 1 log FFU/mL after 0.5 months; less than 1.4 log FFU/mL after 1 month; and about 2 log FFU/mL after 1.5 months of storage at 37° C. This is in striking contrast with the loss of more than 3 log FFU/mL for formulations not containing divalent ions (Table 3).

TABLE 3

Rotavirus liquid formulation: Sucrose 40%, Gelatin 1%, Citric
Acid 0.64%, potassium phosphate dibasic 2.61%, pH 6.3

| Time stored at 37° C. (months) | without divalent ions log FFU/mL | with 4 mM $ZnCl_2$ + 4 mM $CaCl_2$ log FFU/mL |
|---|---|---|
| 0 | 5.99 | 6.10 |
| 0.5 | <3 | 5.34 |
| 1.0 | <3 | 4.56 |
| 1.5 | <3 | 3.97 |

It should be noted that the degree of vaccine stabilization by divalent cations was unexpectedly associated with the high sucrose and pH of the formulation, as the divalent cations by themselves do not confer such degree of stabilization.

Example 2

Liquid Formulation Stability

All formulations containing $ZnCl_2$ and $CaCl_2$ at 4 mM each, presented improved stability (RVLQ-14a to RVLQ-23, except RVLQ-15) at 37° C., as shown in Table 2

The following liquid Rotavirus vaccine formulation was prepared based on the novel complimentary constituent and parameter combinations identified in the experiments above. The formulation consisted of live rotavirus G3 vaccine, citric acid 0.64% w/v; potassium phosphate dibasic, 2.61% w/v; sucrose 40%; gelatin 1% w/v; $CaCl_2$, 4 mM; $ZnCl_2$, 4 mM; pH 6.3. Rotavirus G3 was added to 6.09 log ffu/mL (fluorescence focus units/mL). The stability of the formulation was as follows:

| Time (months) | Titer at 25° C. log ffu/ml | Titer at 37° C. log ffu/ml |
|---|---|---|
| 0.5 | 5.34 | 5.97 |
| 1.0 | 4.56 | 5.95 |
| 1.5 | 3.97 | 5.75 |

Example 3

Spray Drying Rotavirus Formulations

Various formulations and process conditions were used to spray dry viruses. In each case, the spray technique involved combination of the cited formulation with a spray gas at low pressure. The gas/liquid mixture was then sprayed from a nozzle energized with ultrasonic vibrations.

Study 1—A live G3 type Rotavirus was low pressure ultrasonically spray dried under the following conditions:

a) A liquid formulation of 6.87 log ffu/mL (fluorescence focus units/mL) rotavirus in formulation SD01 (7% w/v sucrose, 3% w/v trehalose, 25 mM potassium phosphate buffer (pH 7.0), 0.25% v/v glycerol, 0.02% v/v Pluronic F-68) was prepared. The formulation had a 25% solids content.

b) The formulation was combined at a flow of 0.75 mL/min with a stream of nitrogen gas at 40 psi in a mixing chamber of a nozzle.

c) The nozzle was vibrated at ultrasonic frequencies.

d) The formulation/gas mixture was sprayed into a drying chamber while drying gas flowed into the chamber at 70° C. Drying gas exited the chamber with a 50° C. outlet temperature.

e) Dry particles with a 2.45% moisture content were collected. After reconstitution, the formulation had a zero time titer of 6.94 log ffu/mL (no significant loss of virus viability).

f) To study stability, dry powder particles were held at elevated temperatures and the virus titer monitored. After 6 days at 37° C., the rotavirus had a reconstituted titer of 6.68 log ffu/mL. After 6 days at 45° C., the rotavirus had a reconstituted titer of 6.73 log ffu/mL.

Study 2—A live G3 type Rotavirus was low pressure ultrasonically spray dried under the conditions above except the drying gas inlet temperature was 50° C. and the outlet temperature was 40° C. The resultant powder particles were dried to a moisture content of 3.51% and retained a reconstituted titer of 6.62 log ffu/mL.

Study 3—A live G3 type Rotavirus was low pressure ultrasonically spray dried under the conditions of Study 1 above except the spray gas pressure was 60 PSI, the drying gas inlet temperature was 50° C. and the outlet temperature was 40° C. The resultant powder particles were dried to a moisture content of 2.43% and retained a reconstituted titer of 6.54 log ffu/mL.

Study 4—A live G3 type Rotavirus was low pressure ultrasonically spray dried under the conditions of Study 1 above except the spray gas pressure was 60 PSI, the drying gas inlet temperature was 50° C. and the outlet temperature was 40° C. The resultant powder particles were dried to a moisture content of 2.20% and retained a reconstituted titer of 6.52 log ffu/mL.

Study 5—A live G3 type Rotavirus was low pressure ultrasonically spray dried under the conditions of Study 1 above except the spray gas pressure was 60 PSI, the drying gas inlet temperature was 50° C. and the outlet temperature was 40° C. The liquid formulation SD03 included (7% w/v sucrose, 3% w/v trehalose, 25 mM potassium phosphate buffer (pH 7.0), 0.02% v/v Pluronic F-68) was prepared with a total solids content of 25%. The formulation was low pressure ultrasonically spray dried (to 4.29% moisture), as above, followed by freeze drying 16 hours at 4° C. (to 2.66% moisture). The liquid formulation titer was 6.82 log ffu/mL before spraying. The resultant powder particles retained a reconstituted titer of 6.57 log ffu/mL.

Study 6—A live G3 type Rotavirus was low pressure ultrasonically spray dried under the conditions of Study 1 above except the spray gas pressure was 60 PSI, the drying gas inlet temperature was 50° C. and the outlet temperature was 40° C. The liquid formulation SD02 included (7% w/v sucrose, 3% w/v trehalose, 25 mM potassium phosphate buffer (pH 7.0), 0.5% glycerol, 0.02% v/v Pluronic F-68) was prepared with a total solids content of 25%. The formulation was low pressure ultrasonically spray dried (to 3.33% moisture), as above, followed by freeze drying 16 hours at 4° C. (to 2.26% moisture). The liquid formulation titer was 6.77 log ffu/mL before spraying. The resultant powder particles retained a reconstituted titer of 6.37 log ffu/mL.

Study 7—Spray drying live rotavirus G3 vaccine at high solids content. A live G3 type Rotavirus was low pressure ultrasonically spray dried under the conditions of Study 1 above except the spray gas pressure was 60 PSI, the drying gas inlet temperature was 50° C. and the outlet temperature was 40° C. The virus was formulated with liquid formulation SD01 but to provide a total solids content of 50%.

Example 4

Freeze Drying Rotavirus Formulations

Use of divalent cations, such as zinc ($Zn^{2+}$) and calcium ($Ca^{2+}$), to stabilize calcium carbonate-containing formulations. As was described above for liquid Rotavirus formulations (Table 3), $Zn^{2+}$ and $Ca^{2+}$-containing formulations demonstrated a far superior stability profile compared to those in their absence. In this Example, we demonstrate that their incorporation does not cause instability to the vaccine upon freeze drying. After reconstitution, $Zn^{2+}$- and/or $Ca^{2+}$-containing formulations are expected to demonstrate superior stability, affording a longer window of opportunity to administer the vaccine to patients.

Study 1—A live G1 strain Rotavirus was formulated with varying amounts of sucrose, mannitol and gelatin, as shown in Table 4. The final solids content for all of the formulations examined was 14% (w/v). In addition to the above mentioned components, calcium carbonate ($CaCO_3$) was added to serve as an antacid, and its effect on viral stability at three concentrations were examined; one formulation not containing $CaCO_3$ was prepared as a control to examine the effect of $CaCO_3$ on the stability of rotavirus (formulation F-1). Furthermore, the effects of zinc chloride ($ZnCl_2$) and glycerol were also examined. In all cases, Rotavirus was initially formulated with the soluble components and titrated to 6.0 log ffu/mL. $CaCO_3$ was added to a formulated measles solution immediately prior to placing the samples onto the pre-chilled shelf of the lyophilizer (−50° C.). In order to minimize the amount of settled $CaCO_3$, the suspension was swirled while being cooled in liquid nitrogen ($L_{N2}$). Vials containing 1 mL/ea of Rotavirus formulation were freeze dried according to the cycle shown in Table 5. The resulting freeze dried Rotavirus contained less than 1% residual moisture content.

TABLE 4

Formulation components for freeze dried live G1 rotavirus

| Excipients | Formulation | | | | | | |
|---|---|---|---|---|---|---|---|
| | F-1 | F-2 | F-3 | F-4 | F-5 | F-6 | F-7 |
| Sucrose 7% | | | x | | x | x | x |
| Mannitol 4% | | | x | | x | x | x |
| Mannitol 8% | x | x | | x | | | |
| Gelatin 3% | | | x | | x | x | x |
| Gelatin 6% | x | x | | x | | | |

TABLE 4-continued

Formulation components for freeze dried live G1 rotavirus

| Excipients | F-1 | F-2 | F-3 | F-4 | F-5 | F-6 | F-7 |
| $ZnCl_2$ 0.027% (2 mM) | | | | | | x | |
| $CaCO_3$ 3.36% | | x | x | | | | |
| $CaCO_3$ 10.08% | | | | x | x | x | x |
| Glycerol 0.30% | | | | | | | x |

TABLE 5

| Lyophilization cycle | | | |
|---|---|---|---|
| Step | Temperature (° C.) | Pressure (mTorr) | Time (min) |
| Freezing | −50 | ambient | 140 |
| Primary drying | −35 | 50 | 3850 |
| | 0 | 50 | 485 |
| Secondary drying | 28 | 50 | 1020 |

The stability of freeze dried live G1 strain Rotavirus formulations is shown in Tables 6 and 7. All of the formulations stored at 15° C. demonstrated no statistically significant loss after 3 months of storage (Table 6). The effects of the various excipients on the stability of Rotavirus, however, are clearly discernible from the stability data obtained at 37° C. In the absence of $CaCO_3$ (formulation F-1), the titer of rotavirus decreased at a rate of 0.27 log ffu/ml/month during the first 2 months of storage (Table 7). The titer loss rate increased to 0.49 log ffu/mUmonth upon the addition of 3.36% $CaCO_3$. Upon further increasing the $CaCO_3$ content to 10.08% exacerbated the titer loss rate to 2.91 log ffu/mL/month. The data suggest that Rotavirus is destabilized by the antacid, or that the virus is adsorbed on to the surface of the antacid, decreasing the detectable amount of Rotavirus in the reconstituted media. This deleterious effect of $CaCO_3$ can be reversed by the addition of a stabilizer, such as sucrose. Upon the addition of 7% (w/v) sucrose, while maintaining the final solids content at 14% (w/v), the titer loss rate was minimized to 0.05 log ffu/mL/month (formulation F-3, Table 7) for formulation containing 3.36% $CaCO_3$ after 2 months of storage. Even at the higher $CaCO_3$ concentration of 10.08%, the titer loss rate was minimized to 0.09 log ffu/mL/month by the addition of 7% (w/v) sucrose. The addition of 2 mM $ZnCl_2$ to the latter formulation also had negligible loss after 2 weeks of storage at 37° C. (formulation F-6, Table 7). Thus, the presence of $Zn^{2+}$ did not destabilize the Rotavirus, whether during the freeze drying process or during its storage at an elevated temperature. The presence of 0.3% glycerol also did not demonstrate any loss in titer after 2 weeks of storage at 37° C.

TABLE 6

| Stability of freeze dried live G1 rotavirus formulations at 15° C. The target dose was 6.0 log ffu/mL. Units for values shown below are log ffu/mL. | | | | | | | |
|---|---|---|---|---|---|---|---|
| Time (months) | F-1 | F-2 | F-3 | F-4 | F-5 | F-6 | F-7 |
| 0 | 6.12 ± 0.08 | 5.80 ± 0.03 | 6.10 ± 0.09 | not done | not done | not done | not done |
| 2 | 6.21 ± 0.06 | 5.77 ± 0.19 | 6.26 ± 0.06 | not done | not done | not done | not done |
| 3 | 6.03 ± 0.04 | 5.63 ± 0.07 | 6.11 ± 0.06 | not done | not done | not done | not done |

TABLE 7

| Stability of freeze dried live G1 rotavirus formulations at 37° C. The target dose was 6.0 log ffu/mL. Units for values shown below are log ffu/mL. | | | | | | | |
|---|---|---|---|---|---|---|---|
| Time (months) | F-1 | F-2 | F-3 | F-4 | F-5 | F-6 | F-7 |
| 0 | 6.12 ± 0.08 | 5.80 ± 0.03 | 6.10 ± 0.09 | 5.66 ± 0.04 | 5.89 ± 0.20 | 6.41 ± 0.03 | 5.97 ± 0.11 |
| 0.25 | not done | not done | not done | not done | not done | 6.03 ± 0.12 | 5.92 ± 0.12 |
| 0.5 | 6.17 ± 0.15 | 5.50 ± 0.11 | 6.09 ± 0.07 | 5.45 ± 0.25 | 6.05 ± 0.08 | 6.37 ± 0.04 | 5.89 ± 0.04 |
| 1 | 5.46 ± 0.11 | 5.00 ± 0.19 | 6.01 ± 0.09 | 5.11 ± 0.09 | 5.84 ± 0.15 | not done | not done |
| 2 | 5.68 ± 0.14 | 4.83 ± 0.26 | 6.00 ± 0.05 | <3 | 5.77 ± 0.07 | not done | not done |
| Slope (log ffu/mL/month) | −0.27 ± 0.21 | −0.49 ± 0.12 | −0.05 ± 0.02 | −2.91 ± 0.91 | −0.09 ± 0.07 | −0.16 | −0.08 |

Study 2—A live G1 strain Rotavirus was freeze dried under the processing conditions described in Table 4. The virus was titrated to 6.0 log ffu/mL and formulated with liquid formulation SD01ZC, as described in Example 3, Study 8. Process loss was negligible and the initial titer did not decrease after 2 months of storage at 37° C., or after 3 months of storage at 4° C. and at 25° C. The freeze dried Rotavirus contained 1.4% residual moisture content.

Study 3—A live G1 strain Rotavirus was freeze dried using the processing conditions described in Table 4. The virus was titrated to 6.2 log ffu/mL and formulated with 21.6% (w/v) sucrose, 33 mM potassium phosphate, 15 mM glutamate, 2 mM $ZnCl_2$, 2 mM $CaCl_2$, and 0.8% (w/w) sodium citrate. The solution pH was adjusted to 6.3. Process loss was less than 0.2 log ffu/mL and the initial titer decreased by 0.7 log ffu/mL after 2 months of storage at 37° C. The titer decrease was negligible after 3 months of storage at 4° C. and at 25° C. (<0.1 log ffu/mL). The freeze dried Rotavirus contained 0.6% residual moisture content.

Study 4—A mixture of live Rotavirus strains, G1 and G3, was freeze dried using the processing conditions described in Table 4. Both of the strains were titrated to 6.1 log ffu/mL and formulated with SD01ZC, as described in Example 3, Study 8. The solution pH was adjusted to 6.3.

Study 5—A mixture of live Rotavirus strains, G1, G3, G4, and G9, was freeze dried using the processing conditions described in Table 4. All four strains were titrated to 5.7 log ffu/mL and formulated with SD01ZC, as described in Example 3, Study 8. The solution pH was adjusted to 6.3.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference.

What is claimed is:

1. A liquid vaccine formulation comprising:
   at least one strain of rotavirus at a titer ranging from about $1 \times 10^5$ to about $1 \times 10^8$ pfu/mL;
   a sugar at a concentration ranging from about 10% to about 60% (w/v);
   a phosphate buffer ranging in concentration from about 10 mM to about 2 M;
   a carboxylate ranging in concentration from about 50 mM to about 2 M; and,
   $Zn^{2+}$ in a concentration ranging from 1 to 6 mM.

2. The formulation of claim 1, further comprising $Ca^{2+}$ in a concentration ranging from 1 to 10 mM.

3. The formulation of claim 1, further comprising from about 0.5% to about 5% of gelatin or from about 0.001% to about 2% of a non ionic surfactant.

4. The formulation of claim 1, wherein the carboxylate is selected from the group consisting of: succinate, citrate, fumarate, tartarate, maleate and lactate.

5. The formulation according to claim 1, wherein the sugar is selected from the group consisting of: sucrose, mannitol, lactose, sorbitol, dextrose, fucose, trehalose, polyaspartic acid, inositol hexaphosphate (phytic acid), sialic acid and N-acetylneuraminic acid-lactose.

6. The liquid vaccine formulation of claim 1, further comprising at least one diluent selected from the group consisting of: a tissue culture medium, saline and water.

7. The formulation of claim 1, wherein the concentration of sugar is between about 20% to about 40%; the concentration of phosphate is between about 0.05 to about 0.3 M; and said at least one carboxylate is a citrate or a succinate at a concentration between about 0.05 M and about 0.7 M.

8. The formulation according to claim 1, wherein a pH of the formulation ranges from about pH 5.0 to about pH 8.0.

9. The formulation according to claim 1, wherein the phosphate is selected from the group consisting of: a monophosphate, a polyphosphate and a phosphorylated compound.

10. The formulation according to claim 9, wherein the phosphorylated compounds are phosphorylated sugars or phosphorylated sugar acids.

11. The formulation according to claim 1, wherein the non ionic surfactant is selected from the group consisting of: a polysorbate, a polyoxyethylene alkyl ether, a nonaethylene glycol octylphenyl ether, a hepatethylene glycol octylphenyl ether, a sorbitan trioleate, and a polyoxyethylene-polyoxypropylene block copolymer.

12. The formulation according to claim 1, wherein the surfactant concentration ranges from about 0.005% to about 0.1%.

13. A liquid vaccine formulation comprising:
   at least one strain of rotavirus at a titer ranging from about $1 \times 10^5$ to about $1 \times 10^7$ pfu/mL;
   a sugar at a concentration ranging from about 15% to about 30% (w/v);
   a phosphate buffer ranging in concentration from about 40 mM to about 100 mM;
   a carboxylate ranging in concentration from about 40 mM to about 300 mM: and,
   $Zn^{2+}$ in a concentration ranging from 1 to 6 mM;
   wherein the formulation pH is about pH 6.0 to about pH 6.5.

14. A method of stabilizing a rotavirus, the method comprising:
   cultivating the rotavirus; and,
   formulating the rotavirus in a liquid formulation comprising:
      the rotavirus at a titer ranging from about $1 \times 10^5$ to about $1 \times 10^8$ pfu/mL;
      a sugar at a concentration ranging from about 5% to about 40% (w/v);
      a pH buffer ranging in concentration from about 10 mM to about 2 M at a pH ranging from about pH 5 to about pH 7; and,
      $Zn^{2+}$ in a concentration ranging from 1 to 6 mM.

15. The method of claim 14, wherein the formulation further comprises $Ca^{2+}$ at a concentration ranging 1 to 10 mM.

16. The method of claim 14, wherein the formulation further comprises from about 0.5% to about 5% of gelatin or from about 0.001% to about 2% of an non ionic surfactant.

17. The method of claim 14, wherein the formulation further comprises from about 0.05 M to about 2 M of a carboxylate.

18. The method of claim 14, wherein the sugar is selected from the group consisting of: sucrose, mannitol, lactose, sorbitol, dextrose, fucose, trehalose, polyaspartic acid, inositol hexaphosphate (phytic acid), sialic acid and N-acetyl-neuraminic acid-lactose.

19. The method of claim 14, wherein the buffer comprises a phosphate buffer at a pH ranging from pH 5 to pH 8.

20. The method of claim 14, wherein the $Zn^{2+}$ concentration is about 4 mM.

21. The method of claim 14, further comprising the step of lyophilizing the liquid formulation.

22. The method of claim 14, further comprising the step of spray drying the liquid formulation.

\* \* \* \* \*